(12) United States Patent
Jenney et al.

(10) Patent No.: US 7,231,259 B2
(45) Date of Patent: Jun. 12, 2007

(54) BODY IMPLANTABLE LEAD COMPRISING ELECTRICALLY CONDUCTIVE POLYMER CONDUCTORS

(75) Inventors: Christopher R. Jenney, Valencia, CA (US); Sheldon Williams, Green Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 883 days.

(21) Appl. No.: 10/264,687

(22) Filed: Oct. 4, 2002

(65) Prior Publication Data

US 2004/0068313 A1   Apr. 8, 2004

(51) Int. Cl.
*A61N 1/05* (2006.01)
(52) U.S. Cl. ..................................... 607/116
(58) Field of Classification Search ................ 607/116, 607/119, 122, 125, 126; 600/373, 374, 377
See application file for complete search history.

(56) References Cited

U.S. PATENT DOCUMENTS

| | | | |
|---|---|---|---|
| 3,815,611 A | 6/1974 | Denniston, III | 128/419 D |
| 4,105,732 A | 8/1978 | Slingluff | 264/104 |
| 4,198,991 A | 4/1980 | Harris | 128/784 |
| 4,573,480 A | 3/1986 | Hirschberg | 128/784 |
| 5,029,585 A | 7/1991 | Lieber et al. | 128/642 |
| 5,090,422 A | 2/1992 | Dahl et al. | 128/784 |
| 5,143,089 A | 9/1992 | Alt | 128/784 |
| 5,190,052 A | 3/1993 | Schroeppel | 128/786 |
| 5,211,174 A | 5/1993 | Imran | 128/639 |
| 5,330,520 A | 7/1994 | Maddison et al. | 607/122 |
| 5,330,521 A | 7/1994 | Cohen | 607/122 |
| 5,331,959 A | 7/1994 | Imran | 128/639 |
| 5,385,577 A | 1/1995 | Maurer et al. | 607/41 |
| 5,411,527 A | 5/1995 | Alt | 607/5 |
| 5,411,544 A | 5/1995 | Mar et al. | 607/122 |
| 5,431,681 A | 7/1995 | Helland | 607/4 |
| 5,433,742 A | 7/1995 | Willis | 607/122 |
| 5,476,496 A | 12/1995 | Strandberg et al. | 607/122 |
| 5,534,022 A | 7/1996 | Hoffmann et al. | 607/122 |
| 5,554,176 A * | 9/1996 | Maddison et al. | 607/9 |
| 5,554,178 A | 9/1996 | Dahl et al. | 607/122 |
| 5,554,179 A | 9/1996 | Stroetmann et al. | 607/129 |
| 5,580,699 A | 12/1996 | Layman et al. | 430/311 |
| 5,609,622 A | 3/1997 | Soukup et al. | 607/122 |
| 5,645,580 A | 7/1997 | Moaddeb et al. | 607/122 |
| 5,658,709 A | 8/1997 | Layman et al. | 430/311 |
| 5,681,514 A | 10/1997 | Woody | 264/104 |
| 5,692,926 A * | 12/1997 | Jarl | 439/668 |
| 5,755,766 A * | 5/1998 | Chastain et al. | 607/122 |
| 5,766,527 A | 6/1998 | Schildgen et al. | 264/104 |
| 5,861,023 A | 1/1999 | Vachon | 607/121 |
| 5,902,329 A | 5/1999 | Hoffmann et al. | 607/121 |

(Continued)

*Primary Examiner*—George R. Evanisko

(57) ABSTRACT

A body implantable lead includes a lead body comprising an insulative housing containing at least one conductive polymer conductor terminating within a distal end portion of the lead body at an electrode structure carried by the distal end portion of the lead body. The electrode structure is positioned to contact body tissue to be electrically stimulated and/or sensed. The electrode structure electrically communicates with the at least one conductive polymer conductor by means of an electrically conductive interconnect penetrating the at least one conductive polymer conductor. The at least one conductive polymer conductor terminates within a proximal end portion of the lead body at a terminal contact adapted to be electrically connected to an electrically stimulating/sensing medical device.

Also disclosed are connector assembly, tip electrode and ring electrode structures adapted to be coupled to an implantable lead body containing a conductive polymer conductor.

22 Claims, 10 Drawing Sheets

U.S. PATENT DOCUMENTS

| | | | |
|---|---|---|---|
| 6,254,425 B1 | 7/2001 | Shchervinsky et al. | 439/502 |
| 6,295,474 B1 | 9/2001 | Munshi | 607/121 |
| 6,501,992 B1 | 12/2002 | Belden et al. | 607/122 |
| 6,564,107 B1 * | 5/2003 | Bodner et al. | 607/122 |
| 6,574,514 B2 | 6/2003 | Partridge et al. | 607/126 |
| 6,718,628 B2 | 4/2004 | Munshi | 29/825 |
| 6,801,809 B2 | 10/2004 | Lasket et al. | 607/126 |
| 2002/0111664 A1 | 8/2002 | Bartig et al. | 607/122 |
| 2003/0220677 A1 * | 11/2003 | Doan et al. | 607/122 |
| 2004/0102813 A1 | 5/2004 | Kranz et al. | 607/6 |
| 2004/0186545 A1 | 9/2004 | Rosero et al. | 607/119 |

* cited by examiner

BODY IMPLANTABLE LEAD COMPRISING ELECTRICALLY CONDUCTIVE POLYMER CONDUCTORS

CROSS-REFERENCE TO RELATED APPLICATIONS

This application is related to copending U.S. patent application Ser. No. 10/052,776, filed Jan. 18, 2002, titled "Body Implantable Lead Including One or More Conductive Polymer Electrodes and Methods for Fabricating Same."

FIELD OF THE INVENTION

The present invention relates generally to body implantable leads. More particularly, the invention relates to body implantable, transvenous leads including one or more conductive polymer conductors connecting tissue-stimulating and/or sensing electrodes positioned along a distal portion of the lead with a connector assembly at the proximal end of the lead.

BACKGROUND OF THE INVENTION

A body implantable, transvenous lead may be used to electrically connect a pulse generator, such as a pacemaker, with body tissue, such as that of the heart, to be stimulated. A lead of this kind typically includes a lead body comprising a tubular, flexible insulative sheath or housing of silicone rubber, polyurethane or other suitable biocompatible, biostable polymer. In a conventional bipolar cardiac pacemaker lead having a tip electrode and a ring sensing electrode, a pair of metallic coil conductors arranged coaxially with insulation in between the conductors are carried within the insulative housing. One of the coil conductors connects the pulse generator with the tip electrode while the other coil conductor, somewhat shorter than the first conductor coil, connects the pulse generator with the ring sensing electrode positioned proximally of the tip electrode.

Transvenous pacemaker leads often combine a cardioverting and/or defibrillating capability with the pacing and sensing functions. Thus, besides pacing and sensing electrodes, a transvenous type lead may include along its distal end portion one or more cardioverting and/or defibrillating electrodes for shocking selected tissue, for example, the tissue of the superior vena cava (SVC) or the tissue of the right or left ventricle.

To reduce the outside diameter of transvenous leads, lead bodies comprising multilumen housings have been developed. In place of coil conductors, such multilumen housings may contain multistrand metal cable conductors to connect the pulse generator at the proximal end of the lead with the various stimulating and/or sensing electrodes along the distal end portion of the lead body. In some existing multilumen housing lead bodies, a combination of one or more coil conductors and one or more cable conductors is utilized.

A significant portion of the cost of leads utilizing metallic coil or cable conductors is associated with such metallic conductors that require labor-intensive fabrication processes and expensive termination techniques such as welding or crimping. Further, metallic conductors are subject to fatigue failure, even in coil form. In addition, changing electrode placement and/or spacing or changing the length of the lead requires the modification of several parts of the lead, making lead customization complex and costly.

Conductive polymers have been used in body implantable, tissue stimulation leads. For example, U.S. Pat. No. 5,681,514 discloses a body implantable lead comprising alternating layers of conductive and insulative thermosetting polymers with the conductive polymer layers serving as the electrical conductors of the lead. The lead is fabricated by extruding the alternating conductive/insulative polymer layers through successive, coaxially arranged heated nozzles of increasing outer diameter. The '514 patent describes conductive polymers as including polymers filled with electrically conductive particles, intrinsically conductive polymers, and doped polymers.

Body implantable stimulation leads carrying electrodes made of conductive polymers are also known. For example, the above-mentioned '514 patent describes the formation of conductive polymer tip and ring electrodes during the extrusion process by controlling the extrusion of the various layers independently to selectively expose portions of the conductive polymer, with the exposed portions of the conductive polymer serving as the electrodes. Further, U.S. Pat. No. 5,476,496 discloses a bipolar body implantable pacing lead including inner and outer, coaxial metal coil conductors. The inner coil conductor is electrically connected to a pacing/sensing tip electrode at the distal extremity of the lead. The coils are electrically isolated from each other by a first insulating sleeve disposed between the inner and outer coil conductors. The outer coil conductor is enclosed within a second insulating sleeve. A portion of the second sleeve is made of a conductive polymer engaging the outer coil conductor so as to provide electrical communication between the sleeve and the coil conductor. The conductive polymer portion of the second sleeve functions as the indifferent electrode of the pacing system. Still further, U.S. Pat. No. 3,815,611 discloses an isodiametric body implantable lead incorporating a proximal cardioverting electrode constructed of a conductive, flexible silicone rubber material.

The advantages of providing pacing therapies to the left side heart chambers and to both the right and left heart chambers are well established. For example, in four chamber pacing systems, four pacing leads, typically bipolar leads, are positioned for both pacing and sensing in or on the respective heart chambers. To provide left side stimulation and sensing, leads are transvenously implanted in the coronary sinus region, for example, in a vein such as the great vein or the left posterior ventricular (LPV) vein proximate the left ventricle of the heart. Such placement avoids the risks associated with implanting a lead directly within the left ventricle which can increase the potential for the formation of blood clots which may become dislodged and then carried to the brain where even a small embolism could cause a stroke. (As used herein, the phrase "coronary sinus region" refers to the coronary sinus, great cardiac vein, left marginal vein, left posterior ventricular vein, middle cardiac vein, and/or small cardiac vein or any other vein accessible by way of the coronary sinus.)

The tip electrode of a lead implanted in the coronary sinus region can pace and sense left side ventricular activity. When such a lead includes a ring electrode proximal of the tip electrode and residing in the coronary sinus above the left ventricle closely adjacent to the left atrium of the heart, pacing and sensing of left atrial activity is made possible. Moreover, the lead may include one or more electrodes for the delivery of electrical shocks for terminating tachycardia and/or fibrillation. Such cardioverting and/or defibrillating electrodes may be used by themselves or can be combined with the aforementioned pacing and/or sensing electrodes.

The implantation of a lead through the coronary ostium and into the veins in the coronary sinus region is often difficult because of the extreme curvatures in the coronary vessels, their narrowness, anomalies in the vascular anatomy because of disease, and the number of veins which may communicate with the desired lead feed path. Some currently available leads, and particularly the distal end portions thereof, are too stiff and/or too large in diameter to permit easy maneuvering of the distal end portion within the coronary vessels.

Thus, there is a need for improved body implantable leads that simplify and reduce the costs associated with the conductive path or paths thereof, that facilitate the customization of electrode placement and spacing, and provide the flexibility and small diameters needed to enable the lead to be tracked through the coronary ostium and into the veins of the coronary sinus region for left side pacing, sensing and/or cardioversion/defibrillation.

SUMMARY OF THE INVENTION

In accordance with one specific, exemplary embodiment of the invention, there is provided an implantable lead comprising a longitudinally extending lead body comprising a housing of insulative material, the housing defining at least one longitudinally extending passage containing an electrically conductive polymer conductor extending from a connector assembly carried by a proximal end portion of the lead body to a distal end portion of the lead body. The lead further includes at least one electrode carried by the distal end portion of the lead body, the at least one electrode being adapted to perform one or more of the functions consisting of pacing, sensing, cardioversion and defibrillation. Last, an electrically conductive interconnect provides electrical communication between said conductive polymer conductor and the at least one electrode.

Pursuant to another specific, exemplary embodiment of the invention, there is provided an implantable lead comprising a lead body comprising a multilumen housing of insulative material, the lead body having a proximal end portion and a distal end portion. At least one electrode is carried by the distal end portion of the lead body for performing one or more of the functions consisting of pacing, sensing, cardioversion and defibrillation. At least one of the lumens of the housing contains an electrically conductive polymer conductor extending between a connector assembly on the proximal end portion of the lead body and the distal end portion of the lead body, the electrically conductive polymer conductor within said at least one of the lumens being electrically connected to the at least one electrode.

In accordance with another aspect of the present invention, there is provided a connector assembly adapted to be coupled to the proximal end of an implantable lead body containing a conductive polymer conductor. The connector assembly extends along a longitudinal axis of the lead body and comprises an insulative body disposed concentrically about the longitudinal axis, the insulative body having a distal end and a socket adjacent to the distal end for receiving the proximal end of the lead body. The socket has a transverse end wall carrying at least one interconnect pin having a longitudinally extending distal portion projecting into the socket for penetrating the conductive polymer conductor when the proximal end of the lead body is in place within the socket. The insulative body further has a proximal end carrying a longitudinally extending terminal contact pin, the terminal contact pin being electrically connected to the interconnect pin.

Pursuant to yet another aspect of the invention, there is provided a tip electrode adapted to be coupled to the distal end of an implantable lead body containing a conductive polymer conductor. The tip electrode extends along a longitudinal axis of the lead body and comprises an electrically conductive tube disposed concentrically about the longitudinal axis, the tube defining a socket for receiving the distal end of the lead body. The tube further has a distal extremity including a transverse distal end wall carrying a proximally projecting, electrically conductive interconnect pin extending into the socket for penetrating the conductive polymer conductor when the distal end of the lead body is in place within the socket. A tip electrode body is secured to the distal extremity of the tube in electrical communication therewith.

In accordance with still a further aspect of the present invention, there is provided a ring electrode adapted to be positioned along the outer surface of an outer wall of an implantable lead body containing a conductive polymer conductor. The ring electrode comprises an inner surface adapted to engage the outer surface of the lead body and an interconnect pin projecting inwardly from the inner surface of the ring electrode, the interconnect pin being adapted to pierce the outer wall of the lead body and penetrate the conductive polymer conductor.

BRIEF DESCRIPTION OF THE DRAWINGS

The foregoing and other objects, features and advantages of the invention will become evident to those skilled in the art from the detailed description of the preferred embodiments, below, taken together with the accompanying drawings, in which.

DESCRIPTION OF THE PREFERRED EMBODIMENTS

The following description presents preferred embodiments of the invention representing the best mode contemplated for practicing the invention. This description is not to be taken in a limiting sense but is made merely for the purpose of describing the general principles of the invention whose scope is defined by the appended claims.

Figure 1:
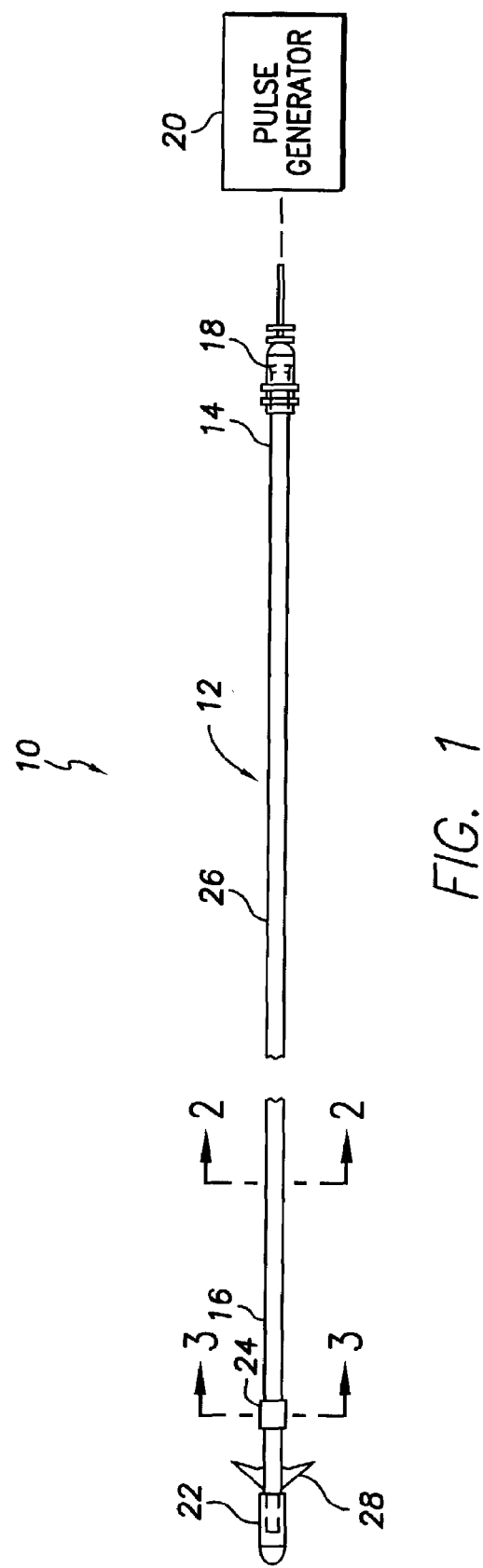
FIG. 1 is a side view of a bipolar body implantable lead in accordance with a first embodiment of the invention.

FIG. 1 shows in simplified, schematic form a passive-fixation bipolar endocardial, body implantable lead 10 in accordance with a first specific, exemplary embodiment of the invention. The lead 10 includes a lead body 12 having a proximal end portion 14 and a distal end portion 16. The proximal end portion 14 of the lead body 12 carries a connector assembly 18, conforming in this example to the IS-1 standard, for coupling the lead body 12 to a receptacle on a pulse generator 20 such as, for example, a pacemaker or an implantable cardioverter/defibrillator (ICD). The distal end portion 16 of the lead body carries a tip electrode 22 and a ring electrode 24 proximal of the tip electrode and spaced apart therefrom. The ring electrode 24 may serve as a pacing/sensing electrode, although it will be evident that it may instead function as a cardioverting and/or defibrillating electrode.

The lead body 12 is adapted to transmit stimulating and/or sensed electrical signals between the connector assembly 18, on the one hand, and the tip and the ring electrodes 22 and 24, on the other.

By way of example and not limitation, the distal end portion 16 of the lead body 12 may have a diameter of about 0.026 inch (2 F) to about 0.131 inch (10 F), with a diameter of about 0.079 (6 F) being preferred, and the ring electrode 24, where it serves a sensing function, may have a diameter of about 0.079 inch (6 F) and a length of about 0.100 inch. The lead body 12 includes a tubular, insulating sheath or housing 26 of a suitable insulative, biocompatible, biostable material such as, for example, silicone rubber, polyurethane or other suitable elastomer, extending the entire length of the lead body 12. The housing 26 includes along the distal end portion of the lead a plurality of rearwardly projecting tines 28 functioning, as is well know in the art, to interlock in the trabeculae within the heart and thereby prevent displacement of the distal end portion 16 once the lead is implanted. Although tines are the preferred anchoring means for purposes of the present invention, it will be understood by those skilled in the art that fins, a screw-in helix, or some other suitable anchoring means may be used instead, including one or more S-shaped bends along the distal end portion, without tines, for anchoring in the vessels of the coronary sinus region.

Figure 3:
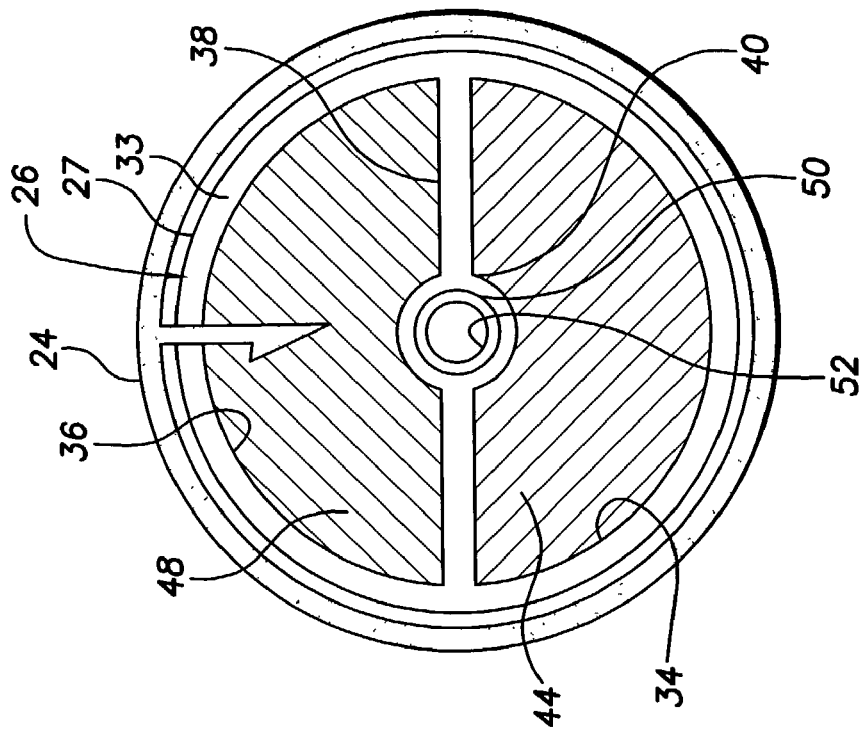
FIG. 3 is a transverse cross section of the lead body of FIG. I as seen along the line 3—3.
Figure 2:
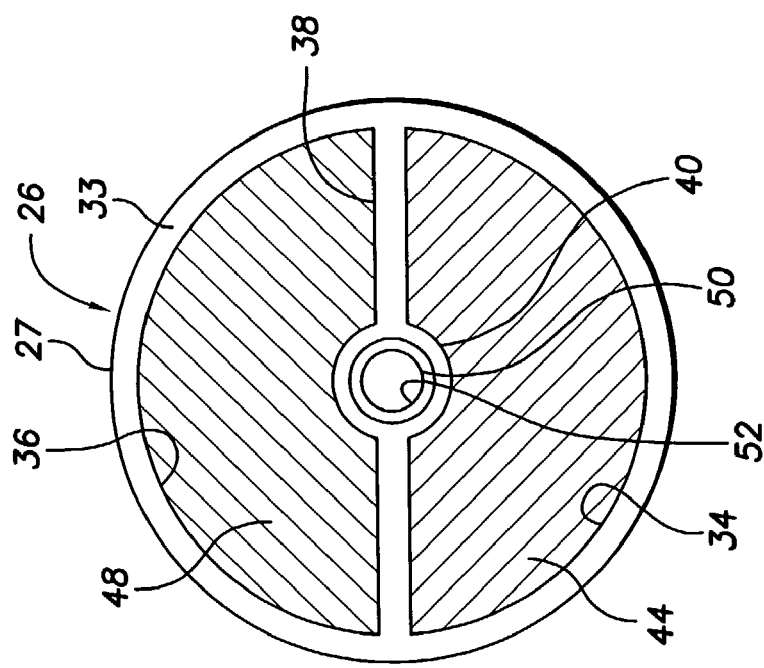
FIG. 2 is a transverse cross section of the lead body of FIG. 1 as seen along the line 2—2.
Figure 4:
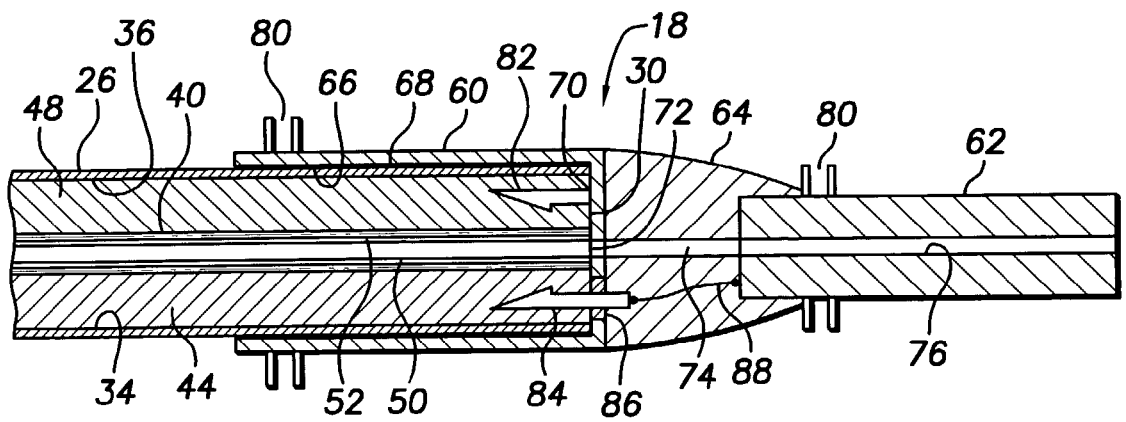
FIG. 4 is an axial cross section of a connector assembly forming part of the lead shown in FIG. 1.
Figure 5:
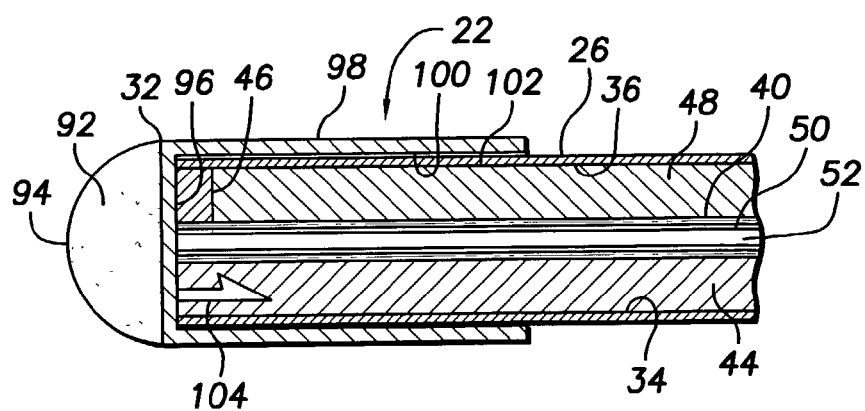
FIG. 5 is an axial cross section of a tip electrode forming part of the lead shown in FIG. 1.

Referring now also to FIGS. 2–5, in the specific, exemplary embodiment under consideration, the housing 26, as seen in FIGS. 4 and 5, has a proximal extremity 30 within the connector assembly 18 and a distal extremity 32 within the tip electrode 22. Further, as best seen in FIGS. 2 and 3, the housing 26 comprises a multilumen structure of preferably uniform, circular cross section, and includes in this example an outer tubular wall 33 and first and second, parallel, longitudinally or axially extending passages in the form of lumens 34 and 36 each having a generally D-shaped cross section. The lumens 34 and 36 are separated by a diametrical insulative partition 38 carrying a small, central, longitudinally extending tube 40 concentric with the tubular wall 33. The entire length of the first lumen 34 is filled with an electrically conductive polymer 44. Similarly, except for a portion adjacent the distal extremity 32 occupied by a short, electrically insulative plug 46, the entire length of the second lumen 36 is filled with an electrically conductive polymer 48.

Conductive polymers of the kind that may be utilized in the present invention fall into two general categories: intrinsically conductive and conductor-filled. Intrinsically conductive polymers include polyacetylene, polypyrrole, and polyanaline, among others. Alternatively, conductor-filled polymers may include presently available materials approved for implantation such as silicone rubber with embedded metallic or carbon particles or powder. Silver filled silicone rubbers of the kind manufactured by NuSil or Specialty Silicone Products, modified so as to be approved for implantation, are of potential utility. An example is silver-coated, nickel-filled silicone rubber sold as NuSil R2637. This material offers the flexibility of silicone rubber and a conductivity similar to MP35N, the current choice for pacemaker lead conductors.

The tube 40 may contain an axially extending, thin walled tube 50 of low friction material such as PTFE, extending the entire length of the housing and defining a central lumen 52.

With reference to FIG. 4, the connector assembly 18 is dimensioned to closely fit within the receptacle of the pulse generator 20 and may be designed to conform to IS1 standards. The connector assembly 18, comprises a tube 60 of electrically conductive material, a tubular connector pin 62 and a body 64 of insulative material joining the tube 60 and the connector pin 62. The tube 60 has an open, distal end or socket 66 for receiving a proximal end 68 of the lead body 12 and a transverse, proximal wall 70 having a central aperture 72. As best seen in FIG. 4, the center lumen 52, the central aperture 72 in the transverse, proximal wall 70 of the tube 60, an axial bore 74 in the insulative connector assembly 64, and an axial bore 76 in the connector pin 62 are all axially aligned.

In accordance with principles well known in the art, one or more sets of ring seals 80 may be attached to the exterior surface of the connector assembly 18 to prevent body fluids from entering the pulse generator receptacle receiving the connector assembly.

Figure 6:
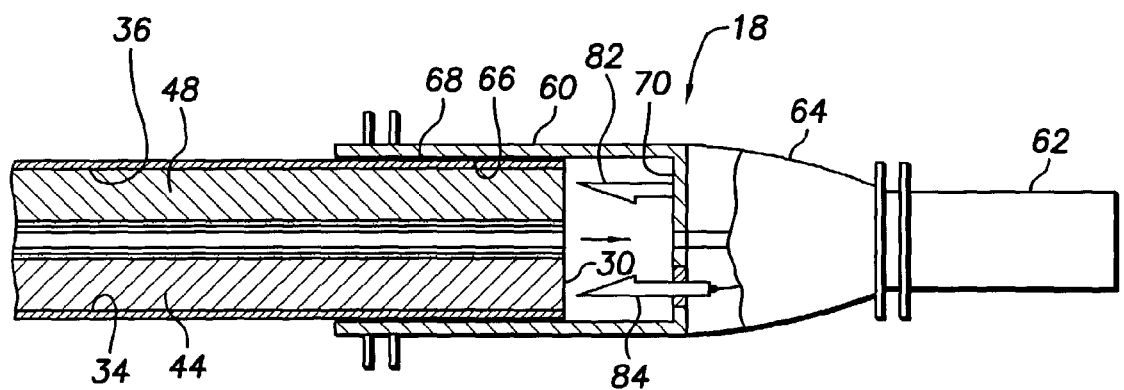
FIG. 6 is an exploded side view, partly in axial cross section, of a connector assembly, along the lines of that shown in FIG. 4, illustrating the manner in which it is attached to an associated lead body.

Mounted on and projecting distally from the transverse wall 70 of the tube 60 are a first, longitudinally extending electrical interconnect pin 82 and a second, longitudinally extending electrical interconnect pin 84. The first pin 82 is attached to the transverse wall by welding or other means assuring a secure, electrically conductive connection. The second pin 84 is supported by the transverse wall 70 of the tube by an insulative insert 86 electrically isolating the second pin from the tube 60. The second pin 84 is electrically connected to the connector pin 62 by a wire 88 within the insulative body 64. It will thus be seen that the lead body 12 and the connector assembly 18 may be readily assembled by pressing the proximal end 68 of the lead body into the socket 66 of the connector assembly tube 60. When the connector assembly 18 is inserted in the receptacle of the pulse generator, separate electrical contacts within the receptacle engaging the tube 60 and connector pin 62 will be in electrical communication with the first and second pins 82 and 84, respectively. Referring now also to FIG. 6, the lead body 12 and the connector assembly 18 are assembled by pushing the proximal end 68 of the lead body 12 into the connector assembly tube socket 66 until the proximal extremity 30 of the lead body engages the transverse wall 70. The lead body is rotationally oriented so that when the proximal end 68 thereof is inserted into the socket 66, the pin 82 penetrates the conductive polymer 48 in the lumen 36 and the second pin 84 penetrates the conductive polymer 44 in the lumen 34. The proximal end 68 and the socket 66 may be provided with matching cross-sectional shapes including, for example, mating flats or a key and keyway, to ensure a single rotational orientation of the end 68 within the socket 66. The distal end of each of the pins 82 and 84 may simply taper to a point or it may have a barb, as shown, to facilitate the full insertion of the lead body end 68 into the tube 60 but resist withdrawal of the lead body once its end is in place within the socket 66. Medical adhesive may be used to further secure the lead body end 68 in place within the tube 60.

Figure 7:
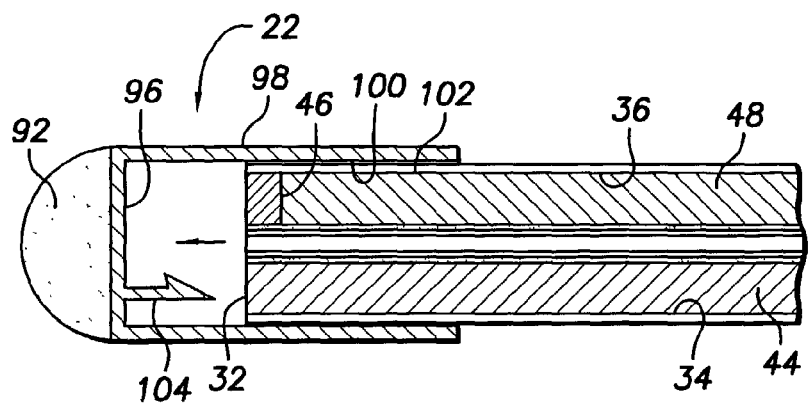
FIG. 7 is an exploded axial cross section view of a tip electrode, along the lines of that shown in FIG. 5, illustrating the manner in which it is attached to an associated lead body.

With reference to FIG. 5, the tip electrode 22 includes a conductive electrode body 92 having an active outer surface 94 adapted to engage the target tissue and to electrically stimulate that tissue and/or sense electrical signals therefrom. The electrode body 92 is conductively bonded to a transverse, distal end wall 96 of an electrically conductive tube 98 having an open proximal end or socket 100 for receiving a distal end 102 of the lead body 12. With reference also to FIG. 7, the distal end 102 of the lead body is inserted into the socket 100 of the tube 98 and advanced until the distal extremity 32 of the lead body engages the transverse wall 96. The lead body is rotationally oriented so that a conductive pin 104 projecting proximally from the transverse wall 96 penetrates the conductive polymer 44 in the lumen 34 of the housing. Electrical continuity is thus established between the connector pin 62 on the connector assembly 18 and the electrode body 92 of the tip electrode 22. The distal end 102 and the tube socket 100 may be provided with matching cross-sectional shapes including, for example, mating flats or a key and keyway, to ensure a single rotational orientation of the end 102 within the tube socket. The conductive polymer 48 in the lumen 36 is electrically isolated from the tube 98 by virtue of the insulative plug 46 in the lumen 36 adjacent to the distal extremity 32. Like the connector assembly 18, the tip electrode 22 is readily coupled to the lead body 12 by pressing the lead body end 102 in place; the end of the pin 104 may taper to a point or it may be barbed, as shown, to facilitate attachment of the tip electrode 22 to the lead body but preventing its withdrawal therefrom. Further, medical adhesive may be used to securely hold the lead body end 102 within the tube 98.

Figure 8:
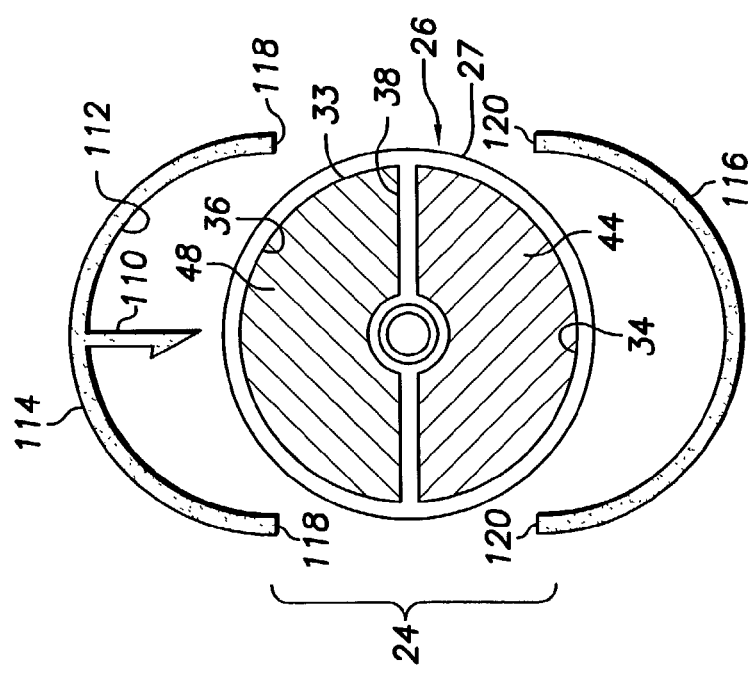
FIG. 8 is a transverse cross section view of a portion of a lead such as that of FIG. 1 showing details of the construction and assembly of a ring electrode in accordance with one embodiment thereof.

The electrically conductive ring electrode 24 is configured to fit closely about the outer surface 27 of the tubular housing 26, as seen in FIG. 3. The ring electrode 24 is electrically coupled to the conductive polymer 48 in the lumen 36 by means of an interconnect pin 110 projecting radially inwardly from an inner surface 112 of the ring electrode to which surface the pin 110 is secured by welding or the like. The pin 110 may simply taper to a point at its inner end or it may be barbed, as shown in the drawing. Electrical continuity is thereby established between the ring electrode 24 and the tube 60 of the connector assembly 18. As shown in FIG. 8, the ring electrode 24 may be formed of a pair of arcuate sections 114 and 116 one of which (114) carries the pin 110 which pierces the side wall 33 of the housing. The arcuate ring sections 114 and 116 are welded or otherwise conductively bonded together at their ends 118 and 120, respectively, following placement of the sections on the housing. It will be appreciated that the design of the ring electrode 24, in combination with the presence of the conductive polymer 48 within essentially the entire length of the lumen 36, permits placement of the ring electrode 24 at any selected location along the length of the distal end portion 16 of the lead body. The lead may thus be customized to accommodate the anatomy of a particular patient. Medical adhesive may be used to further hold the ring electrode in place on the lead body and to seal the puncture made by the pin 110.

Figure 9A:
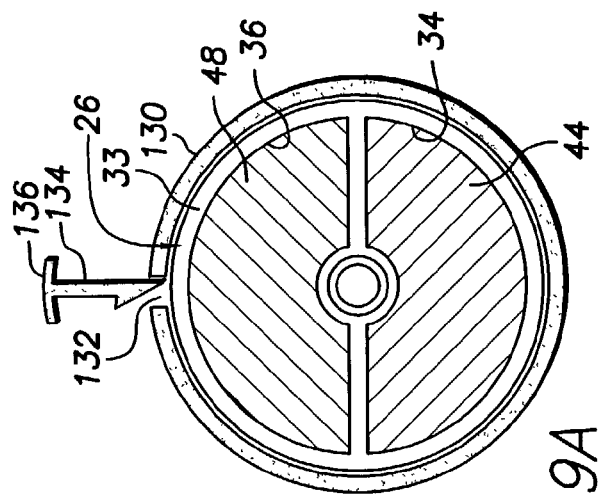
FIGS. 9A and 9B are transverse cross section views of a portion of a lead such as that of FIG. 1 showing details of the construction and assembly of a ring electrode in accordance with another embodiment thereof.
Figure 9B:
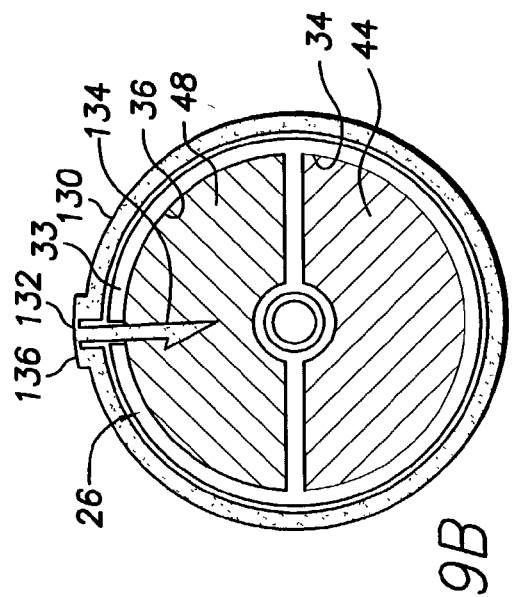

A ring electrode 130, in accordance with an alternative embodiment is shown in FIGS. 9A and 9B. The ring electrode 130 comprises a unitary ring structure having an aperture 132. The ring electrode 130 is attached to the lead body 12 by sliding the electrode to a selected location along the distal end portion 16 of the lead body with the aperture 132 overlying the lumen 36. An electrically conductive interconnect 134, preferably in the form of a pin having an enlarged head 136, is inserted in the aperture 132 and driven through the outer wall 33 of the housing and into the conductive polymer 48 until the enlarged head 136 of the pin engages the outer surface of the ring electrode 130. (FIG. 9B.) The pin 134 may taper to a point or it may be provided with a barbed inner end, as shown. This alternative ring electrode design also permits positioning of the ring electrode at any selected location along the distal end portion of the housing. The headed pin 134 is then used to secure the ring electrode 130 in place and provides an electrically conductive path between the ring electrode 130 and the conductive polymer 48 in the lumen 36, and thereby establishes electrical continuity between the ring electrode 130 and the tube 60 of the connector assembly 18 via the interconnect pin 134.

The trilumen housing 26 preferably comprises an extruded structure and, in accordance with coextrusion techniques well known in the art, the housing 26 and the conductive polymers conductors 44 and 48 occupying the lumens 34 and 36 may be simultaneously formed.

In accordance with well known implantation procedures, a stylet (not shown) is passed through the tubular connector pin 62 and the lumen 52 of the low friction tube 50 within the central tube 40 to enable the implanting physician to orient the distal end portion 16 of the lead and to thereby position the tip electrode 22 under fluoroscopy to a desired location relative to the tissue to be stimulated.

Where both pacing and sensing functions are performed by the tip electrode 22, the conductive polymer 44 provides a bidirectional electrical transmission link between the pulse generator 20 and the tip electrode 22. The conductive polymer 48 connects the tubular terminal 60 on the connector assembly 18 with the ring electrode 24 (or 130) via the electrically conductive pins 82 and 110 (or 134).

It will be appreciated that an array of two or more ring electrodes may be spaced along the distal end portion 16 of the lead, with all of the ring electrodes of the array being connected in parallel to the conductive polymer 48. Such an array of ring electrodes provides a greater effective surface area without unduly compromising the flexibility of the distal end portion of the lead and is particularly useful where the ring electrode array has a cardioverting or defibrillating function, substituting for a single, large, relatively stiff coil electrode.

Figure 10:
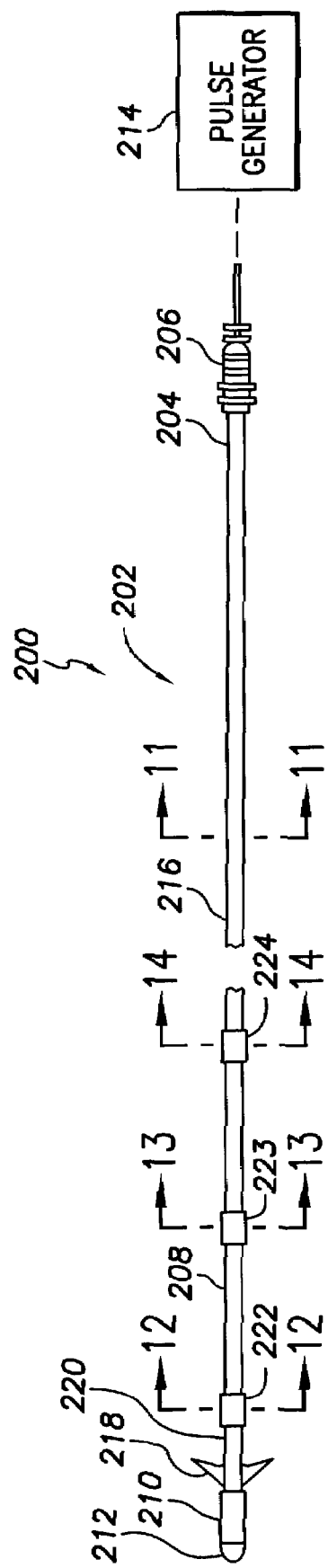
FIG. 10 is a side view of a bipolar body implantable lead in accordance with a second embodiment of the invention.

Turning now to FIG. 10, there is shown a body implantable endocardial lead 200 in accordance with another specific exemplary embodiment of the invention. The lead 200 includes a lead body 202 having a proximal end portion 204 terminating in a connector assembly 206, and a distal end portion 208 including a tip electrode 210 having an active surface 212 adapted to engage body tissue and to electrically stimulate that tissue and/or sense electrical stimuli therefrom. The connector assembly 206 is adapted to be received by a receptacle in a pulse generator 214. The lead body 202 comprises an extruded, isodiametric, multilumen housing 216 fabricated of silicone rubber, polyurethane or other suitable biocompatible, biostable elastomer. The distal end portion 208 of the lead body may include tines 218 or other anchoring means projecting from an outer surface 220 of the housing 216 proximal of the tip electrode. The outer surface 220 of the housing along the distal end portion thereof carries a plurality of ring electrodes each constructed as already described. The specific exemplary embodiment of FIG. 10 incorporates three ring electrodes 222–224; these electrodes are illustrated schematically but it will be understood that the length of each of the electrodes and its placement along the distal end portion of the lead body will be determined by the specific function to be performed by the electrode (pacing, sensing, cardioversion and/or defibrillation), the tissue to be engaged and the particular anatomy of the patient.

As shown in the cross-sections of FIGS. 11–14, the housing 216 comprises an outer tubular wall 228 and a pair of partitions 230 and 232 dividing the housing into four main, sector-shaped, parallel lumens 234–237. The lumens may have equal cross-sectional areas (as shown) or the areas may be different. The housing also includes at the intersection of the partitions 230 and 232 a tube 242 providing a passage for a lead-positioning stylet (not shown). The tube 242 preferably contains a thin wall tubular liner 244 of PTFE or other low friction material defining a central lumen 246 for facilitating the passage of the stylet. In the embodiment under consideration, the stylet guiding tube 242 is centrally located within the housing 216; it will be evident that this need not be the case, and that the tube 242 may be offset from the longitudinal axis of the lead body.

Figure 12:
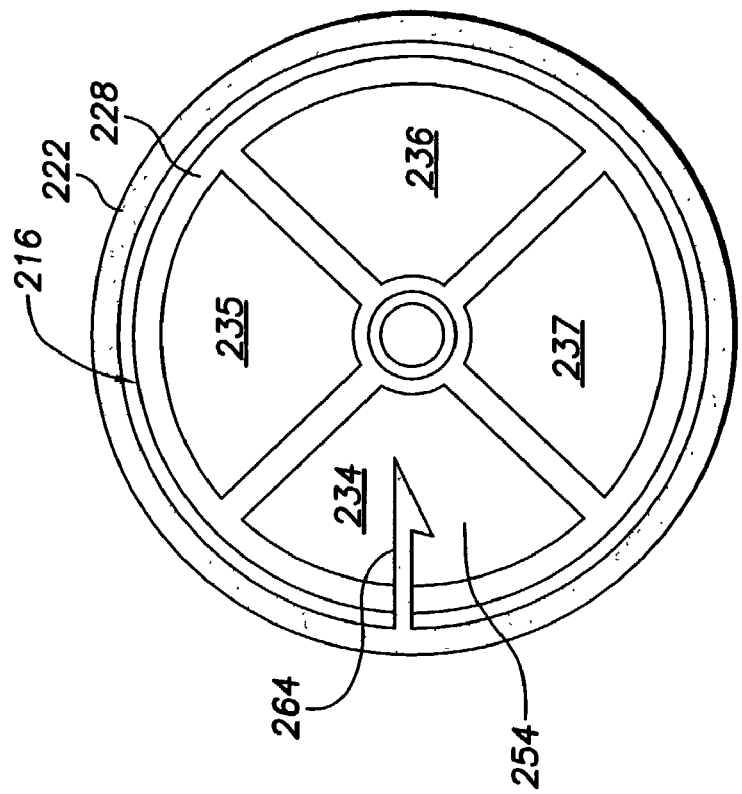
FIG. 12 is a transverse cross section of the lead body of FIG. 10 as seen along the line 12—12.
Figure 11:
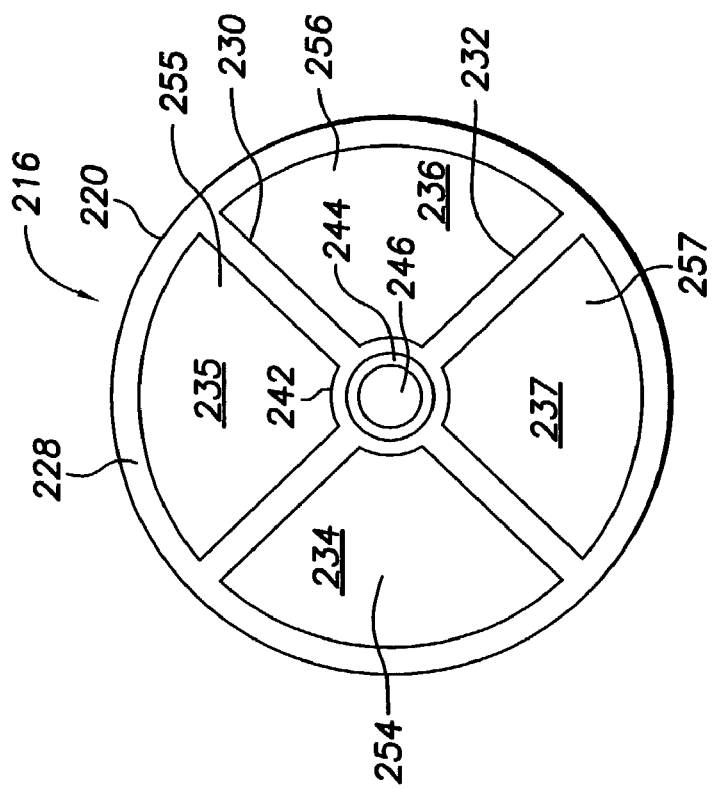
FIG. 11 is a transverse cross section of the lead body of FIG. 10 as seen along the line 11—11.
Figure 14:
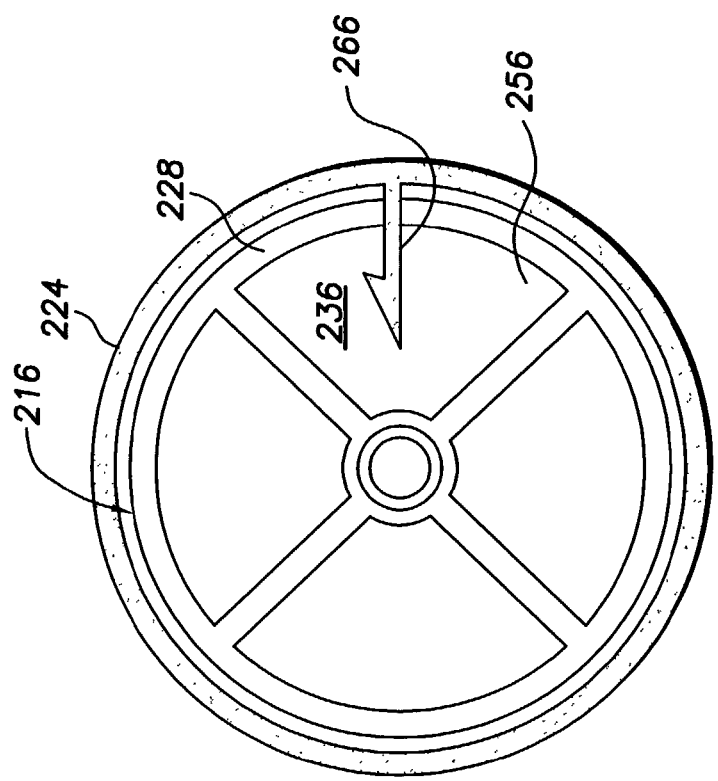
FIG. 14 is a transverse cross section of the lead body of FIG. 10 as seen along the line 14—14.
Figure 13:
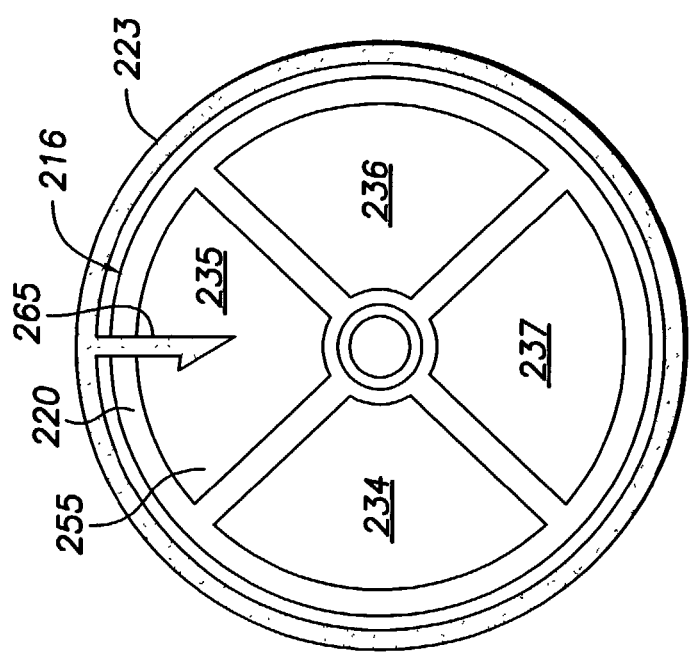
FIG. 13 is a transverse cross section of the lead body of FIG. 10 as seen along the line 12—12.

The main lumens 234–237 are filled with conductive polymers 254–257, respectively, having compositions as already described. As shown in FIGS. 12–14, the ring electrodes 222–224 are in electrical communication with the conductive polymers 254–256 in the lumens 234–236, respectively, by means of interconnect pins 264–266, respectively, unbarbed or barbed, along the lines already described.

Figure 15:
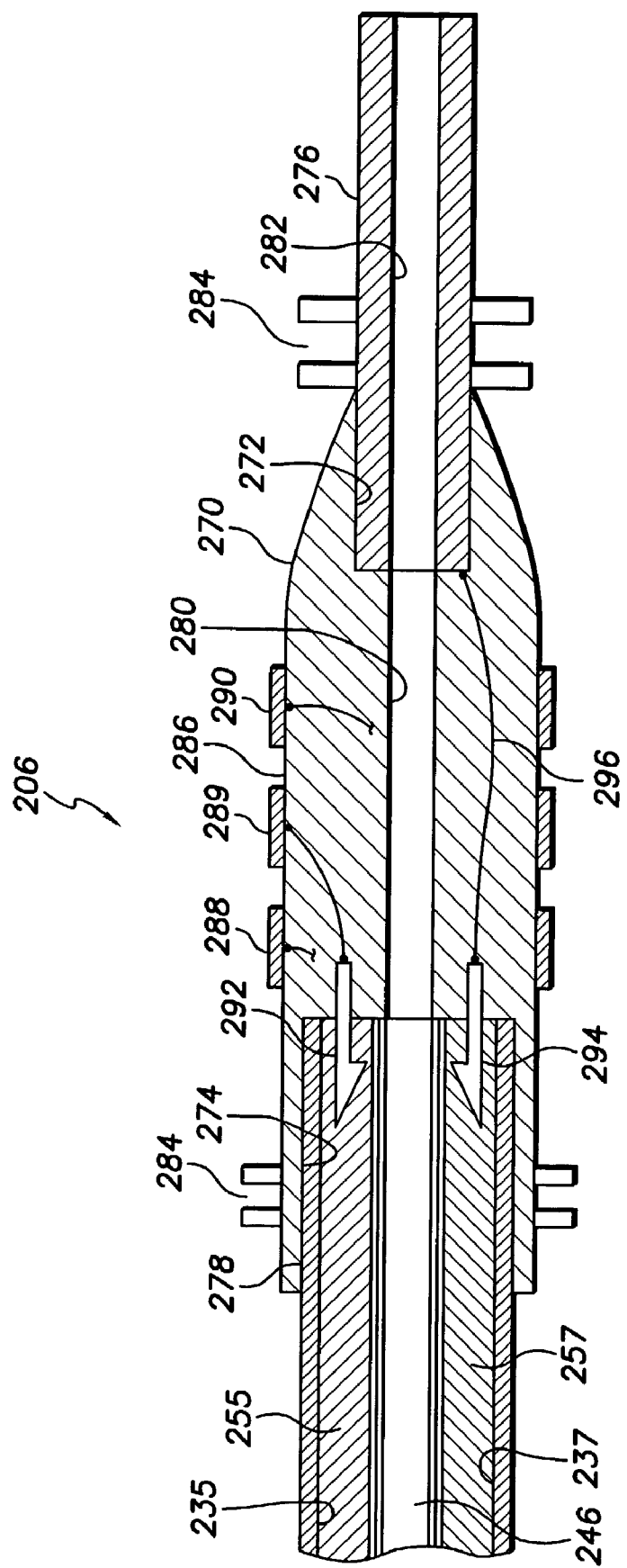
FIG. 15 is an axial cross section of a connector assembly forming part of the lead shown in FIG. 10.

With reference now also to FIG. 15, the connector assembly 206 comprises a generally cylindrical body 270 of insulative material including a proximal counterbore 272 and a distal socket 274 for receiving a tubular connector pin 276 and a proximal end 278 of the lead body 202, respectively. The body 270 includes a central through-bore 280 in axial alignment with a bore 282 of the connector pin 276 and the central lumen 246 within the housing 216. A continuous passage for a lead-positioning stylet is thereby defined. The connector assembly 206 includes longitudinally spaced sets of seals 284. The insulative body 270 has an outer surface 286 carrying three spaced-apart ring terminal contacts 288–290 connected by wires to three axially-extending barbed or unbarbed interconnect pins (of which one, pin 292 is shown) that, with the lead body end 278 fully inserted in the distal counterbore 274, penetrate the conductive polymer conductors 254–256 in the three lumens 234–236 associated with the ring electrodes 222–224, respectively. Electrical continuity is thereby established between the terminal contacts 288–290 and the ring electrodes. A fourth interconnect pin 294 carried by the insulative body 270 and connected to the pin 276 by means of a wire 296, is received by the conductive polymer 257 in the lumen 237.

Figure 16:
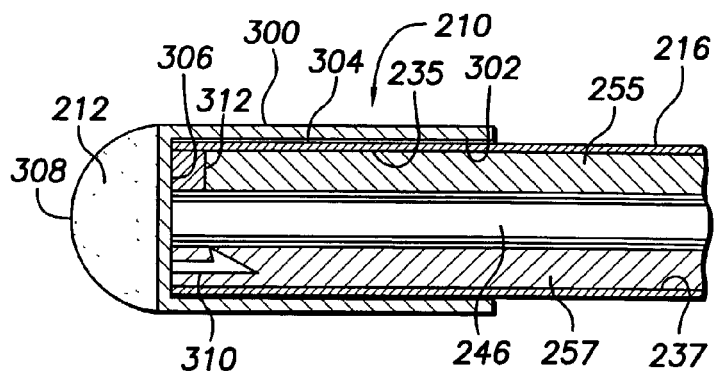
FIG. 16 is an axial cross section of a tip electrode forming part of the lead shown in FIG. 10.

The tip electrode 210, shown in greater detail in FIG. 16, is essentially identical to that of the first embodiment, including a conductive tube 300 having an open end 302 containing a distal end 304 of the lead body 202 and an opposite, closed end 306 conductively bonded to a tip electrode body 308 defining the tip surface 212 and carrying a barbed or unbarbed interconnect pin 310 received within the conductive polymer 257 in the lumen 237 thereby electrically coupling the tip electrode 210 to the connector pin 276. The conductive polymer conductors in the three remaining lumens 234–236 are electrically isolated from the conductive tube 300 by means of insulative plugs, one of which (312) is shown in FIG. 16.

It will be apparent that the housing lumens 234–237 encapsulating their respective conductive polymer conductors may have various cross-sectional configurations so long as those configurations are uniform along the entire length of the housing consistent with the object of being able to coextrude the housing and polymer conductors.

Figure 17:
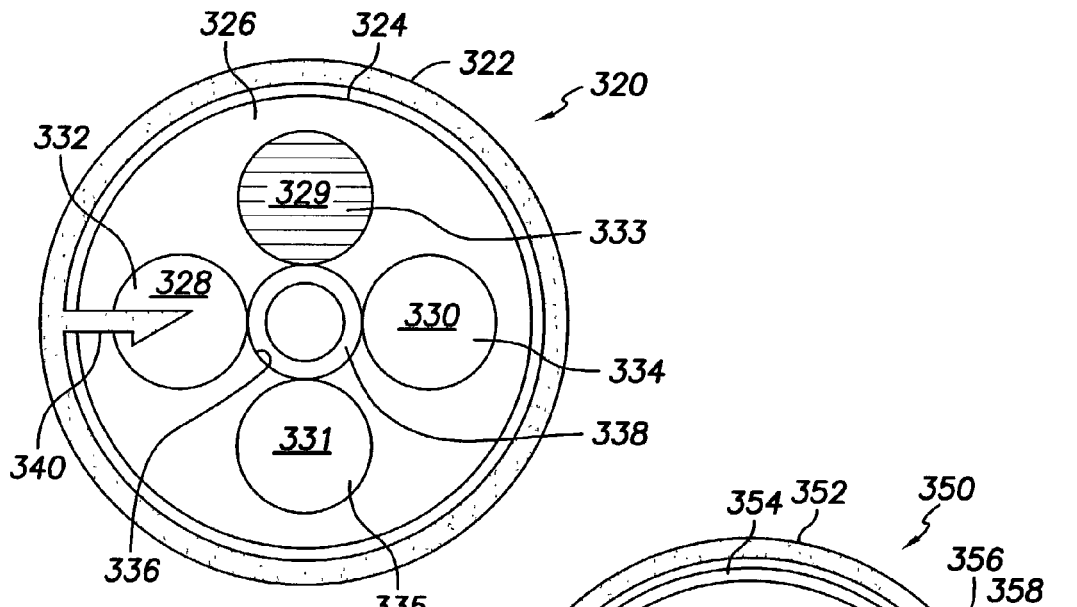
FIG. 17 is a transverse cross section of a portion of a lead in accordance with another embodiment of the invention.

Referring to FIG. 17, there is shown a transverse cross-section of a lead body 320 in accordance with another embodiment of the invention. FIG. 17 shows a cross-section of the lead body 320 as seen along a transverse plane intercepting a ring electrode 322 (exemplary of plural ring electrodes) encircling and engaging an outer surface 324 of a distal end portion of the lead body. The lead body comprises a flexible, tubular, insulative multilumen housing 326 of silicone rubber, polyurethane, or like elastomer, coextruded with a suitable conductive polymer in a single continuous operation to form a structure in which each of the lumens is filled with electrically conductive polymer. In the specific example of FIG. 17, the lead body housing 326 comprises four main parallel lumens 328–331 filled with conductive polymer conductors 332–335, respectively, and a fifth, central lumen 336 which, as before, may enclose a thin wall PTFE tube 338 to form a low friction passage for a lead-positioning stylet. The number of conductive polymer filled lumens may, of course, be varied as well as the cross-sectional shapes and areas thereof, and the compositions of the conductive polymers in the various polymer-containing lumens may be tailored as desired to obtain specific electrically conductive properties.

The ring electrode 322 may be structured as shown, for example, in FIGS. 8, 9A and 9B, and accordingly may include an interconnect pin 340 coupling an inner surface of the ring electrode 322 with the conductive polymer 332 occupying the lumen 328. As before, the interconnect pin 340 may be barbed, as shown, to facilitate penetration of the housing wall and conductive polymer but once installed resisting withdrawal so that the ring electrode is securely anchored at a selected position along the distal end portion of the lead body. Medical adhesive may be applied to further secure the ring electrode 322 and seal the opening in the housing wall made by the pin 340. The conductive polymers 333–335 in the remaining lumens 329–331 may be connected to additional ring electrodes and to a tip electrode in accordance with the principles previously described. The proximal ends of the conductive polymer conductors may be individually connected to terminal contacts and a connector pin on a connector assembly also along the lines already described. Accordingly, in accordance with one example, two additional ring electrodes (not shown) similar to the ring electrode 322 may be provided at selected positions along the distal end portion of the lead body for transmitting pacing, sensing, cardioverting and/or defibrillating signals between the conductor assembly and the various electrodes carried by the distal end portion of the lead body.

Figure 18:
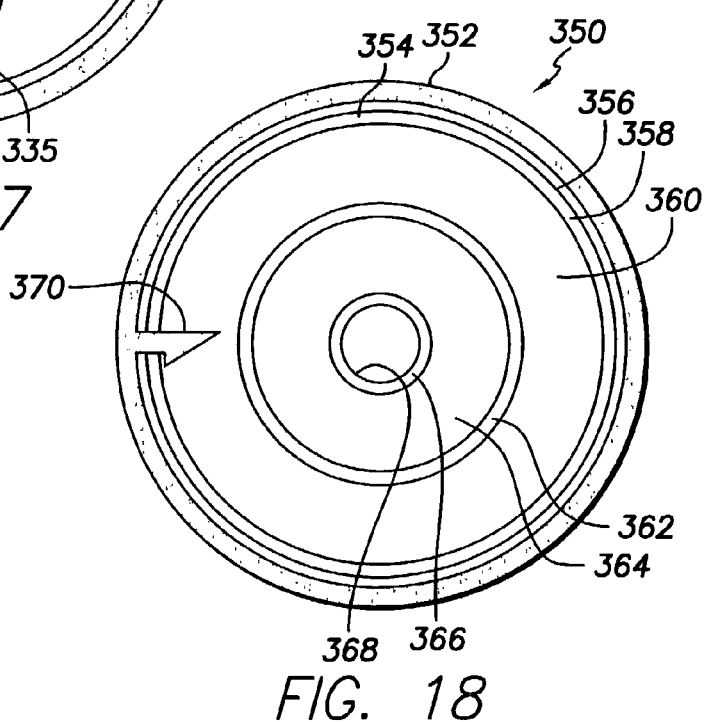
FIG. 18 is a transverse cross section of a portion of a lead in accordance with yet another embodiment of the invention.

Referring to FIG. 18, there is illustrated a transverse cross-section of a lead body 350 in accordance with yet another embodiment of the invention. FIG. 18 shows a cross-section of the lead body as seen along a transverse plane intercepting a ring electrode 352 encircling and engaging the outer surface 354 of the distal end portion of the lead body. The lead body comprises a flexible, tubular, insulative housing 356 of silicone rubber, polyurethane, or the like, coextruded with a suitable conductive polymer in a single, continuous operation to form a coaxial structure comprising multiple, alternating insulative and electrically conductive annular layers. In the specific example of FIG. 18, the lead body 350 comprises in sequence, a first or outer, insulative layer 358; a first conductive polymer layer 360; a second insulative layer 362; a second conductive polymer layer 364; and a third or core insulative layer 366 defining a central lumen 368. The number of layers as well as their thicknesses may, of course, be varied and the compositions of the conductive polymers in the various polymer layers may be tailored as required. As before, the central lumen 368 may be lined with a thin wall, PTFE tube (not shown) to define a low friction passage for a stylet lead positioner. The conductive polymer layers 360 and 364 may be viewed as being contained within coaxial passages defined by the housing 356.

The ring electrode 352 may be structured as shown, for example, in FIGS. 8, 9A and 9B, and includes an interconnect pin 370 coupling an inner surface of the ring electrode 352 with the first conductive layer 360. As before, pin 270 may be barbed shaped to facilitate penetration of the housing wall and conductive polymer but resisting withdrawal so that the ring electrode is securely anchored at a selected position along the distal end portion of the lead body. Another ring electrode (not shown) similar to the electrode 352 may be provided at a selected position along the distal end portion of the lead body in electrical communication with the conductive polymer layer 364. In the example shown in FIG. 18 which has two conductive polymer layers, the second conductive polymer layer 364 may be electrically connected at its distal end to a tip electrode and at its proximal end to a terminal contact on a connector assembly in accordance with the teachings herein.

While several illustrative embodiments of the invention have been shown and described, numerous variations and alternate embodiments will occur to those skilled in the art. Such variations and alternate embodiments are contemplated, and can be made without departing from the spirit and scope of the invention as defined in the appended claims.

What is claimed is:

1. An implantable lead comprising:
a connector assembly;
a longitudinally extending lead body comprising a housing of insulative material, the housing defining at least one longitudinally extending passage containing an electrically conductive polymer conductor extending from the connector assembly carried by a proximal end portion of the lead body to a distal end portion of the lead body;
at least one electrode carried by the distal end portion of the lead body, said at least one electrode being adapted to perform one or more of the functions consisting of pacing, sensing, cardioversion and defibrillation; and
an electrically conductive interconnect providing electrical communication between said conductive polymer conductor and said at least one electrode;
wherein the interconnect comprises a pin having an end penetrating the conductive polymer conductor.

2. The lead of claim 1 in which:
the end of the pin is barbed to facilitate insertion of the pin into the conductive polymer conductor but resist withdrawal therefrom.

3. The lead of claim 1 in which:
the at least one longitudinally extending passage comprises a lumen defined by the housing.

4. The lead of claim 3 further comprising:
a plurality of electrodes carried by the distal end portion of the lead body;
and in which:
the at least one longitudinally extending passage comprises a plurality of parallel lumens, each of said plurality of lumens containing a conductive polymer conductor, an electrically conductive interconnect providing electrical communication between each of the conductive polymer conductors and a corresponding electrode.

5. The lead of claim 4 further comprising:
a longitudinally extending lumen defined by the housing for guiding a lead-positioning stylet.

6. The lead of claim 1 in which:
the housing and the at least one longitudinally extending passage comprise a coaxial structure.

7. The lead of claim 6 further comprising:
a plurality of electrodes carried by the distal end portion of the lead body;
and in which:
the coaxial structure comprises alternating insulative and conductive polymer conductor layers, an electrically conductive interconnect providing electrical communication between each of the conductive polymer conductor layers and a corresponding electrode.

8. The lead of claim 7 further comprising:
a longitudinally extending lumen defined by the housing for guiding a lead-positioning stylet.

9. The lead of claim 8 further comprising:
a low friction liner within the longitudinally extending lumen.

10. The lead of claim 3 in which:
the at least one electrode comprises a tip electrode.

11. The lead of claim 3 in which:
the at least one electrode comprises at least one ring structure.

12. The lead of claim 11 in which:
the at least one ring electrode comprises a clamshell structure comprising at least two arcuate sections disposed about an outer surface of the distal end portion of the housing.

13. The lead of claim 12 in which:
the arcuate ring electrode sections have ends joined by electrically conductive bonds to form a complete ring.

14. The lead of claim 11 in which:
a medical adhesive bonding the at least one ring electrode to an outer surface of the distal end portion of the housing.

15. A body implantable lead comprising:
a lead body comprising an insulative housing;
a first electrode structure carried by a distal end portion of the lead body;
a second electrode structure carried by the distal end portion of the lead body;

a first conductive polymer conductor contained in the insulative housing, the first conductive polymer terminating within a distal end portion of the lead body at the first electrode structure;
a second conductive polymer conductor contained in the insulative housing, the second conductive polymer terminating within the distal end portion of the lead body at the second electrode structure; and
a first electrically conductive interconnect and a second electrically conductive interconnect;
wherein the first and second electrode structure are positioned to contact body tissue to be electrically stimulated and/or sensed, wherein the first and second electrode structure are respectively electrically communicating with the first and second conductive polymer conductor by the first and second electrically conductive interconnect respectively penetrating the first and second conductive polymer conductor, wherein the first conductive polymer conductor terminates within a proximal end portion of the lead body at a terminal contact adapted to be electrically connected to an electrically stimulating/sensing medical device, and wherein the first and second conductive polymer conductor are disposed noncoaxially; and
wherein the electrically conductive interconnect comprises a pin having an end penetrating the first conductive polymer conductor.

16. The lead of claim 15 in which:

the end of the pin is barbed to facilitate insertion of the pin into the first conductive polymer conductor but resist withdrawal therefrom.

17. The lead of claim 15 further comprising:

a longitudinally extending passage defined by the housing, the first conductive polymer conductor contained within the longitudinally extending passage.

18. The lead of claim 17 in which:

the housing and the first conductive polymer conductor comprise a co-extruded structure.

19. The lead of claim 17 in which:

the housing and the at least one longitudinally extending passage comprise a multilumen structure.

20. The lead of claim 15 in which:

the electrode structure comprises a tip electrode.

21. The lead of claim 15 in which:

the electrode structure comprises at least one ring electrode.

22. The lead of claim 15 in which:

the electrode structure comprises a tip electrode and at least one ring electrode.

* * * * *